(12) United States Patent
Chen et al.

(10) Patent No.: US 11,773,056 B2
(45) Date of Patent: Oct. 3, 2023

(54) METHOD FOR PREPARING TAURINE

(71) Applicant: QIANJIANG Yongan Pharmaceutical CO., LTD., Qianjiang (CN)

(72) Inventors: Yong Chen, Qianjiang (CN); Xiquan Fang, Qianjiang (CN); Shaobo Li, Qianjiang (CN); Feng Liu, Qianjiang (CN)

(73) Assignee: Qianjiang Yongan Pharmaceutical CO., LTD., Qianjiang (CN)

( * ) Notice: Subject to any disclaimer, the term of this patent is extended or adjusted under 35 U.S.C. 154(b) by 60 days.

(21) Appl. No.: 17/402,617

(22) Filed: Aug. 16, 2021

(65) Prior Publication Data
US 2022/0281811 A1    Sep. 8, 2022

(30) Foreign Application Priority Data

Mar. 4, 2021 (CN) .......................... 202110240720.5

(51) Int. Cl.
*C07C 303/22* (2006.01)
*C07C 303/44* (2006.01)
*C07C 303/02* (2006.01)
*C07C 303/32* (2006.01)

(52) U.S. Cl.
CPC .......... *C07C 303/22* (2013.01); *C07C 303/02* (2013.01); *C07C 303/32* (2013.01); *C07C 303/44* (2013.01)

(58) Field of Classification Search
None
See application file for complete search history.

(56) References Cited

U.S. PATENT DOCUMENTS

| 9,428,450 B2 | 8/2016 | Hu |
| 9,428,451 B2 | 8/2016 | Hu |
| 10,071,955 B1 * | 9/2018 | Chen .................... B01D 15/362 |

FOREIGN PATENT DOCUMENTS

| CN | 105732440 A | 7/2016 |
| CN | 107056659 A | 8/2017 |
| CN | 109020839 A | 12/2018 |
| CN | 110252395 A | 9/2019 |
| CN | 108329239 B | 2/2021 |
| EP | 3133060 B1 | 3/2019 |

OTHER PUBLICATIONS

Sodium dithionite (downloaded from https://en.wikipedia.org/wiki/Sodium_dithionite on Dec. 8, 2022) (Year: 2022).*
Chen ("Microwave Synthesis of Taurine and Discussion of Reaction Condition" Wuhan Ligong Daxue Xuebao / Wuhan Ligong Daxue Xuebao, 2011, 33(6), p. 40-43), including machine translation (Year: 2011).*

* cited by examiner

*Primary Examiner* — Amy C Bonaparte
(74) *Attorney, Agent, or Firm* — Kilpatrick Townsend & Stockton LLP

(57) ABSTRACT

The present invention discloses a method for preparing taurine. According to the method, ethylene oxide reacts with hydrogen sulfite to generate isethionate, after the isethionate and ammonia are subjected to an ammonolysis reaction under a microwave condition, ammonia removal is conducted to obtain a taurine salt solution, the taurine salt solution is converted into a taurine solution through acidification or ion exchange or ion membrane or heating, and taurine is extracted through concentration and crystallization. According to the present invention, the reaction time can be shortened, and the reaction temperature and pressure can be reduced, thereby achieving high yield and reducing energy consumption.

20 Claims, No Drawings

METHOD FOR PREPARING TAURINE

CROSS-REFERENCES TO RELATED APPLICATIONS

This application claims priority to and benefits of Chinese Patent Application No. 202110240720.5, filed on Mar. 4, 2021, entitled with METHOD FOR PREPARING TAURINE, which is incorporated by reference herein in its entirety for all purposes.

TECHNICAL FIELD

The present invention relates to a method for preparing taurine.

BACKGROUND INFORMATION

Taurine, of which the chemical name is 2-aminoethanesulfonic acid, is a non-protein amino acid essential for the human body, existing in almost all organs of humans and mammals in a free form. The taurine was first found in ox bile, so the taurine is also called taurocholic acid and ethylamine sulfonic acid. The effect of the taurine is different from that of other amino acid. The taurine is not an essential amino acid for constituting protein, but the taurine is essential in the body, which is similar to a body regulatory factor. According to research, it is found that the taurine has anti-inflammatory, antipyretic, analgesic, anticonvulsant and blood pressure lowering effects, and has good effects on infant brain development, nerve conduction, visual function perfection and calcium absorption. Meanwhile, the taurine has many important functions of protecting the heart, preventing and treating cardiovascular and cerebrovascular diseases and the like, has a series of unique functions for the cardiovascular system and can enhance physique and relieve fatigue; therefore, the taurine has high medicinal and medical values and is an important nutrient, which is widely used in the fields of functional beverage, pet food, health-care food, feed, medicine and the like. In addition, the taurine may also serve as a synthetic intermediate of a biochemical reagent and other high added-value products, and is a fine chemical with a wide application value.

The chemical synthesis process route of the taurine mainly includes an ethylene oxide method and an ethanolamine method. The traditional taurine production adopts the ethanolamine method, but this synthesis method has a long reaction period, especially the sulfonation reaction needs to be carried out for 30 hours or above. Meanwhile, the total yield of the taurine is low and the production cost is slightly high, so the method has been gradually eliminated. The current mainstream production process adopts the ethylene oxide method, in which the key reaction step is that sodium isethionate and ammonia are under the harsh reaction conditions of high temperature (200-280° C.) and high pressure (14-21 MPa), and at the same time, the conversion rate is still not high under such high temperature and high pressure conditions. According to DD219023A3, the conversion rate of the sodium taurate in the ammonolysis reaction is only 71%, such that the subsequent extraction process is complex, it is necessary to perform extraction and recrystallization for many times to meet the quality requirement, and the overall process route of ammonolysis and purification is very high in energy consumption cost; moreover, the reaction conditions of high temperature and high pressure make the safety risk of the production process higher.

The main reaction process for preparing the taurine by the ethylene oxide method is as follows:

(1) ethylene oxide, as a starting raw material, and sodium hydrogen sulfite are subjected to an addition reaction to obtain sodium isethionate, wherein the main reaction is:

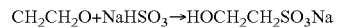

(2) the sodium isethionate is subjected to ammonolysis to obtain sodium taurate; and

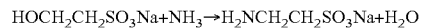

(3) taurine and salt are obtained through acidification or other ways.

U.S. Pat. Nos. 9,428,450B2 and 9,428,451B2 as well as European patent EP3133060B1 introduce a method for circularly producing taurine, which mainly describes that it is necessary to add an alkaline catalyst in the ammonolysis reaction process, a reaction is conducted at the reaction temperature of 150-280° C. and under the pressure from natural pressure to 260 bar, separation is conducted by the solubility difference of taurine and sodium sulfate, but through the description, the reaction conditions are still harsh, and the problem of byproducts is not solved, the operation process is very complex and the energy consumption is too high.

CN109020839A introduces a recycling process for preparing taurine through ammonolysis of sodium isethionate. The content of the taurine crude product is 90%, the sodium sulfate is converted into a sodium silicate product with low requirement on impurities, so that the problem about treatment of the sodium sulfate is solved. In the process method, the temperature and pressure of the ammonolysis are still high, there are many byproducts, the process route is too long and complex, and the energy consumption is high.

Chinese patent CN105732440A discloses that any one or a combination of alkali metal hydroxide, alkali metal carbonate (containing acid carbonate), iron/aluminum series metal salt, NiO/CeO2 and rare earth oxide may be added in the ammonolysis reaction process in which mother liquor is used indiscriminately to serve as a catalyst, and the yield of the sodium taurate may be increased to 90-95%, but the reaction still needs to be carried out at high temperature of 255-265° C under a pressure of 19-20 MPa, and the condition is still harsh.

Chinese patent CN107056659A discloses that in the ammonolysis reaction process, any one or a mixture of any two or more of sodium hydroxide, potassium hydroxide, lithium hydroxide, sodium carbonate, potassium carbonate and lithium carbonate is selected as a catalyst, and at this time, the ammonolysis reaction may be conducted at the temperature of 250-270° C under the pressure of 10-15 MPa. The condition of the patent is slightly mild compared with that in the patent CN105732440A.

CN108329239B introduces a method for preparing taurine from sodium isethionate. The ammonolysis reaction of the sodium isethionate is catalyzed by a molybdate homogenous catalyst, and then the finished product taurine is obtained through the steps of neutralization, crystallization and separation and the like. Compared with the traditional alkaline catalyst, the process can obviously reduce the temperature and pressure of the ammonolysis reaction of the sodium isethionate and shorten the reaction time. However, the biggest problem lies in that a new chemical substance is introduced in the production process, the subsequent separation of the homogenous catalyst and purification are difficult, and at the same time, it is necessary to change regularly, and the production operation is cumbersome. If a better conversation rate is achieved and the reaction temperature is reduced, it is still necessary to prolong the reaction time.

CN110252395A discloses a catalyst for preparation of high-purity taurine. The catalyst is N,N-disubstituted taurine, and the catalyst is added in the ammonolysis step for preparing the taurine. However, the disadvantage is that the new chemical substance is introduced and is difficult to separate from the product, the problem of the reaction time is not solved, and the conversion rate of the taurine is less than 50% after 30-minute reaction.

In summary, the shortcomings of the existing process for preparing the taurine are mainly reflected in the ammonolysis reaction process, the reaction condition needs to be under high temperature and high pressure, the reaction time is too long and the conversion rate is not high. Part of the patent process reduces the reaction condition through the ammonolysis catalyst, but the reaction time is long; meanwhile, the new chemical substance is introduced, which affects the separation and purification of the subsequent products.

BRIEF SUMMARY OF THE INVENTION

To overcome the shortcomings in the prior art, the present invention provides a method for preparing taurine, which can shorten the reaction time and reduce the reaction temperature and pressure, and is high in yield and low in energy consumption.

To achieve the above objective of the present invention, the technical solution of the present invention to solve the above technical problems is as follows:

In the process for producing the taurine by an ethylene oxide method, the core technology of the present invention is that isethionate and ammonia are subjected to an ammonolysis reaction under a microwave condition.

The ammonolysis reaction conducted under the microwave condition is conducted for 0.4-60 min, preferably 0.5-35 min, more preferably 1-10 min, at 50-260° C., preferably 80-200° C., more preferably 100-150° C., under the pressure of 0.1-22 Mpa, preferably 1-10 MPa, more preferably 3-6 MPa. Through optimization of the above reaction condition, compared with the prior art, the reaction time is reduced, the production period is greatly shortened, and the reaction temperature and the reaction pressure may also be obviously reduced.

The ammonolysis reaction conducted under the microwave condition may be completed in an intermittent reaction kettle, or may be a continuous microwave reaction. The microwave frequency may be any suitable working frequency, preferably 915 MHz or 2450 MHz.

In the isethionate and ammonia reaction system of the present invention, all materials belong to polar substances, and the dielectric constant and dipolarity of all the materials are relatively large and the reaction system exists in an ionic state, so the microwave absorption and conduction capability is very high. The microwave may directly activate hydroxyl, water and ammonia in the reaction liquid, thereby accelerating the reaction. After the isethionate reacts with the ammonia to generate a taurine salt, since the microwave makes the reaction be greatly affected by the bond angle and steric hindrance in the case of excessive ammonia, the generated byproducts ditaurine and tritaurine are greatly reduced. Since the medium is heated in the microwave field mainly by two polarization ways such as dipole turning polarization and interfacial polarization, and secondary amine and tertiary amine with low polarity and alcohol with high molecular weight have low capability of absorbing microwave, so the change of producing the ditaurine and the tritaurine is less and even blocked. Therefore, under the reaction condition of slightly excessive ammonia, a quantitative reaction of the isethionate may be achieved. Thus, the reaction is relatively complete, and the residual of the isethionate and the production of byproducts after the reaction are greatly reduced. What is more unexpected is that ammonolysis is conducted under the microwave condition, the purity of the taurine crude product is greatly increased, and the finished product is of a columnar crystal form, so that the crystal form of the taurine finished product is changed fundamentally, the crystal form of the product is more uniform, the granule size is larger, and the agglomeration time of the product may be greatly prolonged.

Through analysis, in the present invention, the effect of the microwave on the chemical reaction is mainly affected by two aspects: a "thermal effect" and a "non-thermal effect".

Microwave heating is different from the general conventional heating method, and the conventional heating is conduction heating from the surface to the inside by the external heat source through heat radiation. The microwave field does not lead to electron polarization and atomic polarization, and the time of the dipole turning polarization and interfacial polarization exactly coincides with the frequency of the microwave. The heating of the medium in the microwave field mainly depends on the two polarization methods. That is, microwave heating is bulk heating of the material caused by dielectric loss in the electromagnetic field. The advantage of this heating is significant and is similar to the high-frequency dielectric heating technology, except that the used working frequency is a microwave frequency band. The microwave heating means that microwave electromagnetic energy is converted into heat energy, and energy is transmitted through space or medium in the form of electromagnetic wave, so that the consumed energy is not much. Therefore, the microwave has the effect of heating materials efficiently and uniformly, thereby achieving the effects of saving energy and accelerating a chemical reaction.

In addition, in the microwave field, molecular dipole acts to perform ultrahigh-speed vibration at $4.9 \times 10^9$ times per second, so that the average energy of molecules is increased, and the reaction temperature and speed are dramatically increased. Under the action of the microwave, all the polar molecules may be regarded as resonance. Because only resonance can transmit the microwave energy to the polar molecules, the microwave has no effect on the nonpolar molecules. A chemical reaction is destructive collision between the molecules, and the microwave accelerates the movement of the polar molecules unprecedentedly, so that the temperature may be rapidly increased due to movement, the destructive power of intermolecular collision is increased unprecedentedly, and the collision time of two molecules and the time of completing a chemical reaction once will not exceed one ten billionth of a second. The addition of the microwave not only increases the collision strength every time, but also certainly increases the collision times per unit time, so the reaction speed is increased. It may be said that the microwave is microscopic superhigh-speed stirring. Under the action of the microwave, the reaction kinetics is changed and the reaction activation energy is reduced, so that the reaction temperature, pressure and time are reduced.

Specifically, a molar ratio of the isethionate to the ammonia is 1:1-1:15, preferably 1:3-1:15, more preferably 1:5-1:10, such that the ammonia ratio of the reaction is reduced and the ammonia content is reduced accordingly.

Specifically, the concentration of the isethionate is 20%-55%, preferably 30%-45%.

The above isethionate may be sodium isethionate, ammonium isethionate, potassium isethionate or lithium isethionate.

Specifically, ammonia may be liquid ammonia, high-concentration ammonia water or gaseous ammonia, and the concentration of the ammonia in a mixed solution is 5%-28%, preferably 10%-25%.

The method for preparing the taurine by the above ammonolysis reaction under the microwave condition may be as follows: ethylene oxide reacts with hydrogen sulfite to generate isethionate, after the isethionate and ammonia are subjected to a microwave ammonolysis reaction, ammonia removal is conducted to obtain a taurine salt solution, the taurine salt solution is converted into a taurine solution through one or more of acidification or ion exchange or ion membrane or heating, and then, taurine is extracted through concentration and crystallization.

The main reaction equations include:

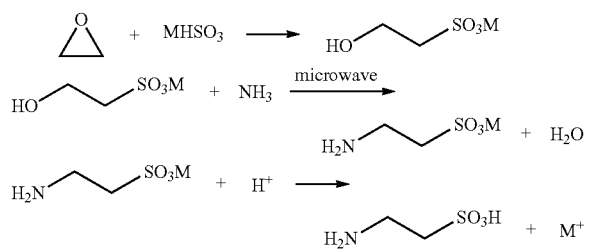

wherein M may be a substance such as sodium, potassium, ammonium, hydrogen and the like capable of forming a cation (a positive ion).

Specifically, the method includes the following steps:
S1: ethylene oxide reacts with a hydrogen sulfite solution to obtain isethionate;
S2: the isethionate obtained in the S1 and ammonia are mixed to obtain reaction liquid;
S3: the reaction liquid in the S2 is subjected to an ammonolysis reaction under the microwave action;
S4: after the ammonolysis reaction, the ammonia is removed, the obtained taurine salt is converted into taurine, and crystallization and separation are conducted to obtain a taurine product; and
S5: recycling mother liquor and returning to the S2 after extracting the taurine product in the S4.

wherein, the hydrogen sulfite in the S1 is sodium hydrogen sulfite, ammonium hydrogen sulfite, potassium hydrogen sulfite or lithium hydrogen sulfite and other metal hydrogen sulfite, preferably sodium hydrogen sulfite and ammonium hydrogen sulfite.

Specifically, the concentration of the hydrogen sulfite solution in the S1 is 9%-50%, and the molar ratio of the hydrogen sulfite to ethylene oxide is 1:0.95 to 1:1.

Specifically, the concentration of the isethionate added in the S2 is 20%-55%, preferably 30%-45%.

Specifically, the molar ratio of the isethionate to the ammonia in the S2 is 1:1-1:15, preferably 1:3-1:15, more preferably 1:5-1:10.

Specifically, the concentration of the ammonia in the reaction liquid obtained by mixing in the S2 is 5%-28%, preferably 10%-25%.

Specifically, in the S3, ammonolysis conducted under microwave may be in an intermittent reaction kettle, or may be a continuous microwave reaction, preferably, the microwave frequency is 915 MHZ or 2450 MHZ.

Specifically, in the S3, the reaction time is 0.4-60 min, preferably 0.5-35 min, more preferably 1-10 min.

Specifically, in the S3, the reaction temperature is 50-260° C., preferably 80-200° C., more preferably 100-150° C.

Specifically, in the S3, the reaction pressure is 0.1-22 MPa, preferably 1-10 MPa, more preferably 3-6 MPa.

Specifically, acidification in the S4 may use sulfuric acid, hydrochloric acid, phosphoric acid, water-soluble carboxylic acid, sulfonic acid or solid acid, etc., preferably sulfuric acid and hydrochloric acid.

Specifically, ion exchange in the S4 is strongly acidic cation exchange resin, weakly acidic cation exchange resin, strongly basic anion exchange resin, weakly basic anion exchange resin, an ion exchange membrane, etc., preferably the weakly acidic cation exchange resin and the ion exchange membrane. (For example, Chinese patent CN201710456576.2, with the title of the invention being "a method for circularly producing taurine with high yield", discloses a treatment method for ion exchange).

Specifically, in the S4, the pH of an aqueous solution after the taurine salt is converted into the taurine is 4-9, preferably 6-8.

Specifically, in the S5, the mother liquor after the taurine product is extracted participates in the reaction in the S3 in the form of an electrolytic ion state. If not all the mother liquor exists in the form of the electrolytic ion state, it is necessary to add any one or a mixture of any two or more of metal salt electrolytes such as sodium hydroxide, potassium hydroxide, lithium hydroxide, sodium carbonate, potassium carbonate, lithium carbonate, sodium sulfate, potassium sulfate and lithium sulfate, preferably sodium hydroxide or sodium sulfate, before the mother liquor is recycled to the S2 or in the S2.

The detection result shows that the finished product taurine obtained according to the above method is of a columnar crystal form.

Compared with the traditional production process, the present invention has the following beneficial effects:
1. The method of the present invention adopts a microwave technology, and has the advantages of high reaction speed, high efficiency, less energy loss and low energy consumption.
2. According to the present invention, the taurine is prepared by the ethylene oxide method, and the taurine is directly prepared without introducing new chemical raw materials, so the method of the present invention has the advantages of short reaction time, high selectivity, high yield, simplicity and high efficiency.
3. According to the present invention, the reaction process is accelerated and the reaction is more complete, and meanwhile, the byproduct only contains a tiny amount of ditaurine and tritaurine, even does not contain ditaurine and tritaurine, and the total yield of the taurine after indiscriminate use reaches 95% or above, even 99% or above.
4. The taurine obtained by the method of the present invention is of a columnar crystal form, and the product granules are larger, and the agglomeration time of the product is obviously prolonged.
5. According to the present invention, the reaction condition is milder, the reaction safety is improved and the safety risk is reduced.

DETAILED DESCRIPTION OF THE INVENTION

The specific content of the present invention is further described in detail by the following specific embodiments, and the examples are only used to explain the present invention, but not to limit the scope of the present invention.

To illustrate the technical effect of the preparation method of the present invention, examples are given below. The raw materials used in the following embodiments are all commercially available products unless otherwise specified, the methods used are all conventional methods unless otherwise specified, and unless otherwise specified, the material content refers to mass volume percentage. A high-pressure closed microwave reactor used in the embodiments is existing equipment and the working frequency is selected as 2450 MHZ, but other suitable working frequencies are not limited. Aftertreatment refers to the above step S4, and the taurine salt is converted into the taurine by any methods which are not limited. The following embodiments select the ion exchange resin treatment method.

Embodiment 1

0.16 mol of sodium isethionate was dissolved in 125 ml (2.21 mol) of ammonia water of 30%, then the solution was added into a high-pressure closed microwave reactor to be subjected to a reaction at 230° C., 200° C. and 150° C. respectively for 0.5 minute, ammonia was removed after the reaction, taurine was extracted through aftertreatment, and mother liquor after purification was used indiscriminately in the ammonolysis reaction again. The results are shown in Table 1.

TABLE 1

Data of microwave reaction for 0.5 minute at different reaction temperatures

| Serial number | Microwave reaction time min | Microwave reaction temperature ° C. | Microwave reaction pressure MPa | Yield of sodium taurate | Total yield of taurine after indiscriminate use | Residual content of sodium isethionate |
|---|---|---|---|---|---|---|
| 1 | 0.5 | 230 | 15 | 93.83% | 96.24% | 0.25% |
| 2 | 0.5 | 200 | 10 | 92.97% | 95.86% | 0.35% |
| 3 | 0.5 | 150 | 6 | 92.11% | 95.11% | 0.40% |

The above experimental results show that the reaction time is set as 0.5 min, the pressure is set between 6 MPa and 15 MPa and the temperature is set between 150° C. and 230° C., the yield of the sodium taurate exceeds 92%, and the residual quantity of the sodium isethionate is less than 0.4%; therefore, the reaction time is greatly shortened, and the reaction temperature and the reaction pressure are reduced.

Embodiment 2

0.16 mol of sodium isethionate was dissolved in 125 ml of ammonia water of 30%, then the solution was added into a high-pressure closed microwave reactor to be subjected to a reaction at 230° C., 200° C., 150° C. and 100° C. respectively for 1 min, ammonia was removed after the reaction, taurine was extracted through aftertreatment, and mother liquor after purification was used indiscriminately in the ammonolysis reaction again. The results are shown in Table 2.

TABLE 2

Data of microwave reaction for 1 minute under different temperatures and pressures

| Serial number | Microwave reaction time min | Microwave reaction temperature ° C. | Microwave reaction pressure MPa | Yield of sodium taurate | Total yield of taurine after indiscriminate use | Residual content of sodium isethionate |
|---|---|---|---|---|---|---|
| 1 | 1 | 230 | 15 | 96.82% | 97.57% | 0.20% |
| 2 | 1 | 200 | 10 | 96.40% | 97.40% | 0.28% |
| 3 | 1 | 150 | 6 | 95.54% | 97.39% | 0.35% |
| 4 | 1 | 100 | 3 | 95.11% | 97.78% | 0.40% |

The above experimental results show that the reaction time is set as 1 minute, the pressure is set between 3 MPa and 15 MPa and the temperature is set between 100° C. and 230° C., the yield of the sodium taurate exceeds 95%, and the residual quantity of the sodium isethionate is less than 0.4%; therefore, it indicates that the reaction is complete, the reaction time is greatly shortened, and the reaction temperature and the reaction pressure are reduced. Meanwhile, it also indicates that the ammonolysis reaction does not need to be conducted at the reaction temperature of 150° C. or above under the reaction pressure of 6 MPa or above, and a very high yield can also be obtained.

Embodiment 3

0.16 mol of sodium isethionate was dissolved in 125 ml of ammonia water of 30%, then the solution was added into a high-pressure closed microwave reactor to be subjected to a reaction at 230° C., 200° C., 150° C., 100° C., 80° C. and 50° C. respectively for 10 min, ammonia was removed after the reaction, taurine was extracted through aftertreatment, and mother liquor after purification was used indiscriminately in the ammonolysis reaction again. The results are shown in Table 3.

TABLE 3

Data of microwave reaction for 10 minutes under different temperatures and pressures

| Serial number | Microwave reaction time min | Microwave reaction temperature ° C. | Microwave reaction pressure MPa | Yield of sodium taurate | Total yield of taurine after indiscriminate use | Residual content of sodium isethionate |
|---|---|---|---|---|---|---|
| 1 | 10 | 230 | 15 | 96.40% | 97.26% | <0.1% |
| 2 | 10 | 200 | 10 | 97.25% | 97.98% | <0.1% |
| 3 | 10 | 150 | 6 | 97.68% | 98.01% | <0.1% |
| 4 | 10 | 100 | 3 | 97.25% | 97.32% | <0.1% |
| 5 | 10 | 80 | 1 | 96.0% | 97.5% | <0.1% |
| 6 | 10 | 50 | 0.1 | 95.01% | 97.68% | <0.1% |

The above experimental results show that the reaction time is set as 10 minutes, the pressure is set between 3 MPa and 15 MPa and the temperature is set between 100° C. and 230° C., the yield of the sodium taurate exceeds 95%, and the residual quantity of the sodium isethionate is less than 0.1%; therefore, the reaction time is greatly shortened, and the reaction temperature and the reaction pressure are reduced. Meanwhile, it also indicates that under the condition of the reaction time, the yield of the sodium taurate is basically the same and exceeds 97% at the reaction temperature of 100° C. to 200° C. and under the pressure of 3 MPa to 10 MPa, and the total yield of the taurine after indiscriminate use also exceeds 97% and the reaction is complete.

Embodiment 4

0.16 mol of sodium isethionate was dissolved in 125 ml of ammonia water of 30%, then the solution was added into a high-pressure closed microwave reactor to be subjected to a reaction at 230° C., 200° C., 150° C. and 100° C. respectively for 35 min, ammonia was removed after the reaction, taurine was extracted through aftertreatment, and mother liquor after purification was used indiscriminately in the ammonolysis reaction again. The results are shown in Table 4.

TABLE 4

Data of microwave reaction for 35 minutes at different temperatures

| Serial number | Microwave reaction time min | Microwave reaction temperature ° C. | Microwave reaction pressure MPa | Yield of sodium taurate | Total yield of taurine after indiscriminate use | Residual content of sodium isethionate |
|---|---|---|---|---|---|---|
| 1 | 35 | 230 | 15 | 89.97% | 96.17% | <0.1% |
| 2 | 35 | 200 | 10 | 90.83% | 96.69% | <0.1% |
| 3 | 35 | 150 | 6 | 93.40% | 97.09% | <0.1% |
| 4 | 35 | 100 | 3 | 95.11% | 96.75% | <0.1% |

The above experimental results show that the reaction time is set as 35 minutes, the pressure is set between 3 MPa and 15 MPa and the temperature is set between 100° C. and 230° C., and the residual quantity of the sodium isethionate is less than 0.1%. Compared with the shorter reaction time in the embodiments 1, 2, 3 and 5, the yield of the sodium taurine is reduced overall.

It is also found that after the reaction time reaches a certain degree, the lower the reaction temperature is, the higher the yield of the taurine is. That is, when the reaction time is increased to a certain degree and the reaction temperature is 100° C., compared with the higher temperature such as 150° C., 200° C. and the like, the yield of the sodium taurine is higher.

Embodiment 5

(1) 0.16 mol of sodium isethionate was added into 2.21 mol, 1.76 mol, 0.88 mol and 0.44 mol of ammonia, respectively, a certain amount of water was added, then each solution was added into a high-pressure closed microwave reactor to be subjected to a reaction at 150° C. and under the reaction pressure of 6 MPa for 5 minutes, ammonia was removed after the reaction, the taurine was extracted through aftertreatment, and mother liquor after purification was used indiscriminately in the ammonolysis reaction again. The results are shown in Table 5 (serial numbers 1-4).

(2) 0.16 mol of sodium isethionate was added into 1.76 mol and 0.8 mol of ammonia, respectively, a certain amount of water was added, then each solution was added into a high-pressure closed microwave reactor to be subjected to a reaction at 100° C. and under the reaction pressure of 6 MPa for 5 minutes, ammonia was removed after the reaction, the taurine was extracted through aftertreatment, and mother liquor after purification was used indiscriminately in the ammonolysis reaction again. The results are shown in Table 5 (serial numbers 5-6).

TABLE 5

Data of reaction for 5 minutes at different ammonia ratios and concentrations

| Serial number | Microwave reaction time min | Microwave reaction temperature ° C. | Ammonia/sodium isethionate (molar ratio) | Yield of sodium taurate | Total yield of taurine after indiscriminate use | Residual content of sodium isethionate |
|---|---|---|---|---|---|---|
| 1 | 5 | 150 | 14 | 98.54% | 99.04% | <0.1% |
| 2 | 5 | 150 | 11 | 98.11% | 98.41% | <0.1% |
| 3 | 5 | 150 | 6 | 97.68% | 99.18% | <0.1% |
| 4 | 5 | 150 | 3 | 92.11% | 93.45% | <0.1% |
| 5 | 5 | 100 | 11 | 98.13% | 98.5% | <0.1% |
| 6 | 5 | 100 | 5 | 97.65% | 99.05% | <0.1% |

The above experimental results show that when the reaction time is set as 5 minutes and the temperature is 150° C., the reaction effect is better when the molar ratio of ammonia to sodium isethionate exceeds 1:3, and the yield of the sodium taurate may reach 97.65% when the molar ratio is 1:5.

As can be seen from the experimental result of different microwave reaction time in the embodiments 1-5, the result of the reaction for 5 minutes is that the residual quantity of the sodium isethionate is low and the reaction is very complete. As comparison between 1 minute and 5 minutes, the reaction yield shows an increasing tendency; when the reaction time is 10 minutes, the yield of the taurine has been slightly reduced; and when the reaction time is 35 minutes, the yield is reduced obviously. Therefore, it indicates that the ammonolysis reaction under microwave is very fast and the reaction time may be greatly reduced.

Embodiment 6

Comparative experiment of crystal forms of the products obtained by different processes:
(1) In the sodium taurate solution obtained in each group of experiment in the above embodiments 1-5, treatment was conducted by an ion exchange method after ammonia removal to obtain a taurine solution, concentration and crystallization were conducted to obtain a taurine crude product, then the crude product was decolored, recrystallized, separated and dried to obtain a finished product taurine, and mother liquor after centrifugation may be recycled and crystallized together with the crude product. The crystal form of the finished product taurine was sieved, and the result shows that the taurine is of the columnar crystal form. Two groups of experiment data with the serial numbers 1 and 2 in the embodiment 5 are taken as examples for description, as shown in Table 6.

(2) According to the conventional production process, sodium isethionate (1 mol), sodium hydroxide and ammonia (14 mol) were mixed and heated to 250° C. in a high-pressure reaction kettle, a reaction was conducted under the reaction pressure of 15 MPa for 60 minutes to prepare a sodium taurate solution, ion exchange treatment was conducted after ammonia removal to obtain a taurine solution, concentration and crystallization were conducted to obtain a taurine crude product, the crude product was decolored and recrystallized, separation and drying were conducted to obtain a finished product taurine, and mother liquor after centrifugation may be recycled and crystallized together with the crude product. The crystal form of the finished product taurine was sieved, and the specific data is shown in Table 6.

TABLE 6

Product crystal form data

| Serial number | Less than 40-mesh | 40-60-mesh | 60-80-mesh | 80-100-mesh | 100-120-mesh | 120-150-mesh | More than 150-mesh | Appearance | note |
|---|---|---|---|---|---|---|---|---|---|
| 1 | 43.60% | 19.60% | 7.20% | 14.50% | 6.00% | 5.30% | 3.30% | Columnar | Microwave reaction |
| 2 | 49.80% | 17.30% | 7.30% | 9.10% | 5.70% | 4.80% | 5.90% | Columnar | Microwave reaction |
| 3 | 28.40% | 18.80% | 9.60% | 19.80% | 8.30% | 6.80% | 7.80% | Needle-like | Conventional reaction |

It can be seen from the above experimental result that the crystal form of the finished product taurine obtained by the ammonolysis reaction under the microwave condition is columnar, and the finished product taurine obtained by the prior art is of a needle-like crystal form.

Embodiment 7

Comparative example: comparative experiment using a conventional catalyst 0.16 mol of sodium isethionate is dissolved into 125 ml of ammonia of 30%, 0.02 mol of sodium hydroxide was added, and after mixing, the mixture was added into a high-pressure closed microwave reactor to be subjected to a reaction at 220° C. for 30 minutes, 60 minutes and 90 minutes respectively. The result of the ammonolysis reaction is as follows and the result is shown in Table 7.

TABLE 7

Comparative reaction using the conventional catalyst at different time

| Serial number | Conventional reaction time min | Conventional reaction temperature ° C. | Conventional reaction pressure MPa | Yield of sodium taurate | Molar quantity of sodium hydroxide (mol) | Residual content of sodium isethionate |
|---|---|---|---|---|---|---|
| 1 | 30 | 220 | 12 | 43.0% | 0.015 | 19.80% |
| 2 | 60 | 220 | 12 | 54.0% | 0.015 | 15.60% |
| 3 | 90 | 220 | 12 | 91.0% | 0.015 | 3.50% |

It can be seen from the above experiment that according to the preparation method for adding the catalyst in the ammonolysis reaction in the prior art, when the reaction temperature is 220° C. and the reaction pressure is 12 MPa, the yield increases along with the increase of the reaction time. When the reaction time is set as 30 minutes, the yield of the sodium taurate is 43%; and when the reaction time is set as 90 minutes, the yield of the sodium taurate only reaches 91%.

It can be clearly seen from the above embodiments that the patent method of the present invention can obviously increase the ammonolysis yield, the byproduct is obviously reduced and the reaction is more complete; meanwhile, the time, temperature and pressure required by the reaction are greatly reduced, and when the reaction time is 1-10 minutes, the total yield of the taurine may reach 95% or above. Furthermore, the crystal form of the finished product taurine is a columnar crystal form, which has been changed fundamentally, and the columnar granules are larger and firmer, so that the problem of short agglomeration time of the product is solved. The patent method of the present invention is a chemical process method which is green, environmentally friendly, simple and efficient.

Finally, it should be noted that the foregoing embodiments are only used to explain the technical solutions of the present invention, and are not intended to limit the present invention. Although the present invention is described in detail with reference to the foregoing embodiments, those of ordinary skill in the art should understand that they can still modify the technical solutions described in the foregoing embodiments, or replace the preparation reaction condition, or make equivalent substitutions on some technical features therein. These modifications or substitutions do not make the essence of the corresponding technical solutions deviate from the spirit and scope of the technical solutions of the embodiments of the present invention.

What is claimed is:

1. A method for preparing taurine, comprising:
in a production process of taurine by an ethylene oxide method, subjecting isethionate and ammonia to an ammonolysis reaction under a microwave condition, obtaining a taurate and converting the taurate to a finished taurine product.

2. The method for preparing the taurine according to claim 1, wherein the ammonolysis reaction conducted under the microwave condition is conducted for 0.4-60 min, at 50-260° C., under the pressure of 0.1-22 MPa.

3. The method for preparing the taurine according to claim 1, wherein the ammonolysis reaction conducted under the microwave condition is conducted for 0.5-35 min, at 80-200° C., under the pressure of 1-10 MPa.

4. The method for preparing the taurine according to claim 1, wherein the ammonolysis reaction conducted under the microwave condition is conducted for 1-10 min, at 100-150° C., under the pressure of 3-6 MPa.

5. The method for preparing the taurine according to claim 1, wherein the ammonolysis reaction conducted under the microwave condition is conducted for 0.5 min, at 150-230° C., under the pressure of 6-15 MPa.

6. The method for preparing the taurine according to claim 1, wherein the ammonolysis reaction conducted under the microwave condition is conducted for 1 min, at 100-230° C., under the pressure of 3-15 MPa.

7. The method for preparing the taurine according to claim 1, wherein the ammonolysis reaction conducted under the microwave condition is conducted for 10 min, at 100-230° C., under the pressure of 3-15 MPa.

8. The method for preparing the taurine according to claim 1, wherein the ammonolysis reaction conducted under the microwave condition is conducted for 5 min, at 100-150° C., under the pressure of 6 MPa.

9. The method for preparing the taurine according to claim 1, wherein a molar ratio of the isethionate to the ammonia is 1:1-1:15.

10. The method for preparing the taurine according to claim 1, wherein a molar ratio of the isethionate to the ammonia is 1:3-1:15.

11. The method for preparing the taurine according to claim 1, wherein a molar ratio of the isethionate to the ammonia is 1:5-1:10.

12. The method for preparing the taurine according to claim 9, wherein the concentration of the isethionate is 20 m/v % - 55 m/v %.

13. The method for preparing the taurine according to claim 9, wherein the concentration of the isethionate is 30 m/v % - 45 m/v %.

14. The method for preparing the taurine according to claim 12, wherein the concentration of the ammonia is 5 m/v % - 28 m/v %.

15. The method for preparing the taurine according to claim 12, wherein the concentration of the ammonia is 10 m/v % - 25 m/v %.

16. The method for preparing the taurine according to claim 1, wherein the isethionate is sodium isethionate, ammonium isethionate, potassium isethionate or lithium isethionate.

17. The method for preparing the taurine according to claim 1, wherein the ammonolysis reaction conducted under the microwave condition is completed in an intermittent reaction kettle, or is a continuous microwave reaction.

18. The method for preparing the taurine according to claim 1, wherein the obtained finished taurine product is of a columnar crystal form.

19. The method for preparing the taurine according to claim 1, comprising the following steps:
S1: reacting ethylene oxide with a hydrogen sulfite solution to obtain the isethionate;

S2: mixing the isethionate obtained in the S1 and ammonia to obtain a reaction liquid;

S3: subjecting the reaction liquid in the S2 to an ammonolysis reaction under the microwave action;

S4: after the ammonolysis reaction, removing the excess ammonia, converting the obtained taurine salt into taurine, and conducting crystallization and separation to obtain a taurine product and a mother liquor; and S5: recycling the mother liquor to the S2.

20. The method for preparing the taurine according to claim 19, wherein the taurine salt is converted into the taurine through acidification, ion exchange, contact with an ion membrane, or heating.

* * * * *